United States Patent [19]

Tachibana et al.

[11] Patent Number: 5,262,087
[45] Date of Patent: Nov. 16, 1993

[54] WATER-IN-OIL TYPE EMULSIFIED COMPOSITION

[75] Inventors: Kiyomi Tachibana, Suginami; Hiroshi Yoshioka, Shinagawa, both of Japan

[73] Assignee: Kose Corporation, Tokyo, Japan

[21] Appl. No.: 876,399

[22] Filed: Apr. 30, 1992

[30] Foreign Application Priority Data

May 1, 1991 [JP] Japan .................. 3-099962

[51] Int. Cl.$^5$ .............. A61K 31/78; B01J 13/00; C08L 83/08; C08L 83/12
[52] U.S. Cl. ................. 252/309; 106/287.13; 106/287.14; 252/315.1; 252/315.4; 424/78.03; 524/865
[58] Field of Search ............ 252/308, 309, 315.1, 252/315.4; 106/287.13, 287.14; 524/865; 528/32; 514/937, 944; 424/78.03

[56] References Cited

U.S. PATENT DOCUMENTS

| | | | |
|---|---|---|---|
| 3,575,910 | 4/1971 | Thomas | 528/32 X |
| 4,122,029 | 10/1978 | Gee et al. | 252/309 |
| 4,133,938 | 1/1979 | Bingham | 106/287.14 X |
| 4,231,917 | 11/1980 | Zeldin et al. | 106/287.14 X |
| 4,698,178 | 10/1987 | Hüttinger et al. | 252/309 |
| 4,720,353 | 1/1988 | Bell | 252/309 |
| 4,782,095 | 11/1988 | Gum | 514/937 |
| 4,814,184 | 3/1989 | Aguadisch et al. | 424/486 |
| 4,834,972 | 5/1989 | Chang | 424/78 |
| 4,990,561 | 2/1991 | Yoshioka | 524/763 |
| 5,015,469 | 5/1991 | Yoneyama et al. | 252/308 X |
| 5,061,481 | 10/1991 | Suzuki et al. | 514/937 X |

FOREIGN PATENT DOCUMENTS

59-126478 7/1984 Japan .

*Primary Examiner*—Richard D. Lovering
*Attorney, Agent, or Firm*—Bacon & Thomas

[57] ABSTRACT

A water-in-oil type emulsified composition comprises (A) 30–60 wt. % of an oil-phase component comprising 60–100 wt. % of a silicone gel composition composed of a wax composition obtained by polymerizing a methylpolysiloxane (meth)acrylate macromonomer and a radical polymerizable monomer and a low-viscosity silicone oil, (B) 0.1–10 wt. % of a polyoxyalkylene-modified organopolysiloxane surfactant of the general formula (1) or (2):

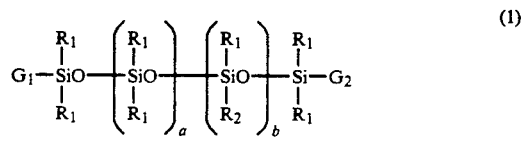

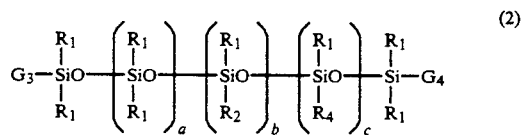

and (C) 5–69.9 wt. % of water.

13 Claims, No Drawings

WATER-IN-OIL TYPE EMULSIFIED COMPOSITION

BACKGROUND OF THE INVENTION i) Field of the Invention

This invention relates to water-in-oil type emulsified compositions, and more specifically to water-in-oil type emulsified compositions which are excellent in stability with time, form a highly water-repellant film on the skin, give users a pleasant feel upon use and are particularly suitable for use as cosmetic preparations or the like.

ii) Description of the Background Art

Emulsified compositions are classified roughly into an oil-in-water type (O/W type) and a water-in-oil type (W/O type). Of these, the water-in-oil type emulsified compositions have been used widely in skin care products owing to their excellent properties such that the affinity with the skin is good and the surface of the skin is hence covered with an oil film to prevent the transpiration of water, so that they avoid skin dryness and have a treating effect to the skin, and as base materials for cosmetic preparations such as makeup preparations or for medicaments because they are excellent in water repellency and keep makeup looking fresh, as compared with the oil-in-water type emulsified compositions.

These water-in-oil type emulsified compositions greatly affect the user's feel when applied to the skin because their oily bases form an external phase of an emulsion as a continuous phase. In order to give users a more pleasant feel upon use, various attempts have heretofore been made. For example, it has been practiced to change the oily base from hydrocarbon oil to ester oil, glyceride or silicone oil so as to reduce the oily feeling to the touch and to improve the conformability to the skin. In particular, it has been attempted to incorporate a large amount of a silicone oil as an oily base in water-in-oil type emulsified cosmetics because it provides cosmetic preparations which are dry and nonsticky to the touch, give users an agreeable feel upon use and have excellent water repellency.

However, when the silicone oil is used in a large amount as an oily base, a surfactant becomes hard to stably orient because of its poor compatibility with the surfactant, so that the surfactant tends to separate and cohere, and it hence is difficult to obtain a water-in-oil type emulsified composition good in stability. For this reason, various kinds of surfactants have been investigated with a view toward using them as an emulsifier. However, wholly satisfactory surfactants have not been found yet. For example, polyoxyalkylene-modified organopolysiloxane is known as an emulsifier used in usual water-in-oil type emulsified compositions. Even when this organopolysiloxane has been used in an emulsion containing a large amount of a silicone oil, it has however been difficult to obtain the emulsion with good stability. Besides, it has been attempted to thicken and gelatinize an oil phase in order to stabilize the emulsion state. However, thickening and gelling agents effective in the case where the silicone oil is contained in a large amount have scarecely been obtained.

As described above, any water-in-oil type emulsified compositions containing a large amount of a silicone oil and satisfying both feel upon use and emulsion stability have not been provided yet.

SUMMARY OF THE INVENTION

In view of the foregoing circumstances, the present inventors have carried out an extensive investigation. As a result, it has been found that when a silicone gel composition composed of a specific wax composition and a low-viscosity silicone oil is contained in an oil-phase component, and a specific polyoxyalkylene-modified organopolysiloxane is used as an emulsifier, an excellent water-in-oil type emulsified composition, which is superb in stability with time, gives users a pleasant feel upon use and is high in usefulness as a base material for cosmetic preparations, can be obtained, leading to completion of the present invention.

In an aspect of this invention, there is thus provided a water-in-oil type emulsified composition comprising the following components (A) through (C):

(A) 30-60 wt. % of an oil-phase component comprising 60-100 wt. % of a silicone gel composition composed of:

(a) a wax composition obtained by polymerizing a mixture of at least one macromonomer selected from the group consisting of methylpolysiloxane (meth)acrylate macromonomers, which contain one (meth)acrylate group and at least three methylsiloxy groups per molecule, and at least one radical polymerizable monomer copolymerizable with the macromonomers in the presence of dimethylpolysiloxane and/or methylphenylpolysiloxane and an organic wax using a radical generator, said wax composition being dispersed in a low-viscosity silicone oil; and (b) a low-viscosity silicone oil;

(B) 0.1-10 wt. % of a polyoxyalkylene-modified organopolysiloxane surfactant represented by the general formula (1) or (2):

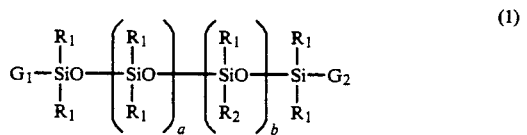

wherein $R_1$ denotes an alkyl group having 1-5 carbon atoms or a phenyl group, $R_2$ represents $-Q_1O(C_2H_4O)_m(C_3H_6O)_nR_3$, in which $Q_1$ means a divalent hydrocarbon group having 1-5 carbon atoms, $R_3$ denotes a hydrogen atom, an alkyl group having 1-5 carbon atoms or an acetyl group, and m and n stand for an integer of one or more and zero or more, respectively, $G_1$ and $G_2$ may be identical to or different from each other and mean individually $R_1$ or $R_2$, and a and b stand for an integer of zero or more, respectively, with the proviso that in case of b being zero, at least one of $G_1$ and $G_2$ means $R_2$:

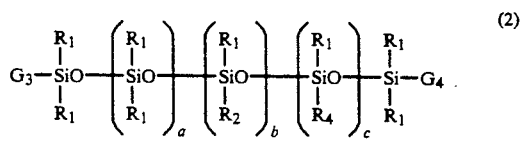

wherein $R_1$, $R_2$, a and b have the same meaning as defined above, $R_4$ represents an alkyl group having 2-20 carbon atoms or $-Q_2OR_5$, in which $Q_2$ means a divalent hydrocarbon group having 1-4 carbon atoms, $R_5$ denotes a hydrocarbon group having 8-30 carbon atoms, $G_3$ and $G_4$ may be identical to or different from each other and mean individual $R_1$, $R_2$ or $R_4$, and c stands for an integer of zero or more, with the proviso that in case of b being zero, at least one of $G_3$ and $G_4$ means $R_2$, and in case of c being zero, at least one of $G_3$ and $G_4$ means $R_4$; and (C) 5-69.9 wt. % of water.

The water-in-oil type emulsified compositions according to this invention are excellent in that they exhibit superb stability with time even when a large amount of a silicone oil is used, give a pleasant dry feel upon use because they feel neither oily nor sticky, and permit the formation of a film which is high in water repellency on the skin.

These and other objects and advantages of the present invention will become apparent from the preferred embodiments of this invention, which will be described subsequently in detail.

DETAILED DESCRIPTION OF THE INVENTION AND PREFERRED EMBODIMENTS

In this invention, the dimethylpolysiloxane or methylphenylpolysiloxane, which is the first component constituting the wax composition of (a) in the component (A), is represented by the following general formula:

$$(CH_3)_p \cdot (C_6H_5)_q SiO_{(4-p-q)/2}$$

wherein p and q satisfy the following relationship:

$$1 \leq p \leq 3, \ 0 \leq q \leq 1.7, \ 1.5 < p+q \leq 3,$$

and may be linear, cyclic or branched. This component may also be a mixture of at least two compounds different in molecular structure and/or molecular weight. Polysiloxanes ranging from those having a viscosity as low as 1 cSt to high polymers in the form of a raw rubber may suitably be used as necessary for the end application intended.

The second component, i.e., organic wax, is a natural or synthetic, organic solid substance. Illustrative waxes are led by animal waxes such as beeswax and wool wax, and vegetable waxes such as carnauba wax and Japan wax, and include petroleum waxes such as montan wax, paraffin wax, petrolatum and microcrystalline wax, and synthetic waxes such as polyethylene wax.

The third component of the wax composition is a graft copolymer obtained by copolymerizing a mixture of at least one macromonomer selected from the group consisting of methylpolysiloxane (meth)acrylate macromonomers, which contain one (meth)acrylate group and at least three methylsiloxy groups per molecule, and at least one radical polymerizable monomer copolymerizable with the macromonomers. In order to obtain a composition high in stability without lowering compatibilizing ability, the weight fraction of the methylpolysiloxane (meth)acrylate macromonomer may preferably be 5-90 wt. %. In this invention, no particular limitation is imposed on the methylpolysiloxane (meth)acrylate macromonomer so for as it has one (meth)acrylate group and at least three methylsiloxy groups in its molecule. A typical macromonomer may be represented by the following general formula (3):

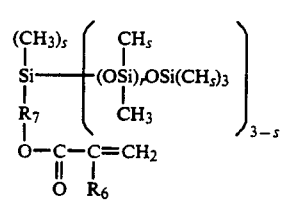

(3)

wherein s stands for 0, 1 or 2, r means an average polymerization degree and is 0-200 when s is 0, 1-200 when s is 1, or 2-200 when s is 2, $R_6$ denotes a hydrogen atom or a methyl group, and $R_7$ means a divalent hydrocarbon group having 1-6 carbon atoms, which may be interrupted by an oxygen atom.

The compound represented by the general formula (3) can be synthesized by the reaction of a living polymer disclosed in, for example, Japanese Patent Application Laid-Open No. 126478/1984, which has been obtained by the anionic polymerization of a cyclic siloxane, and a (meth)acrylate-containing chlorosilane compound. As specific examples of the compound represented by the general formula (3), may be mentioned the following compounds:

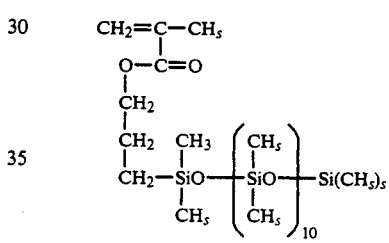

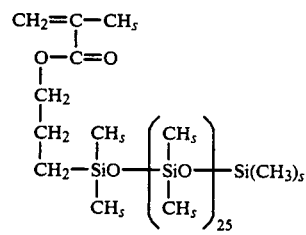

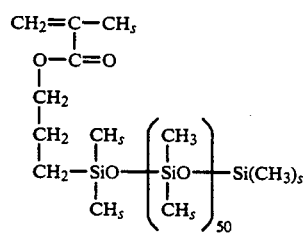

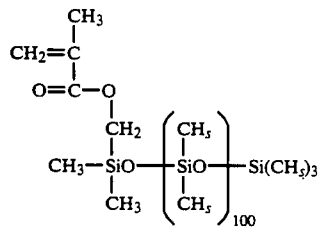

5
-continued
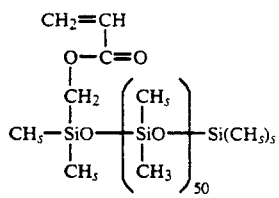
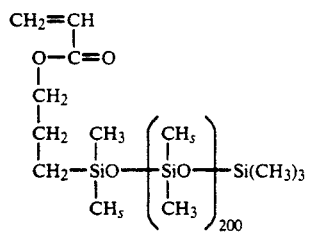
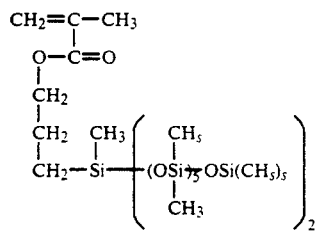
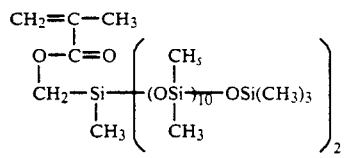
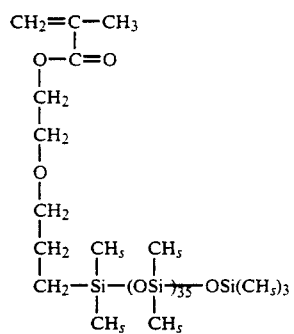
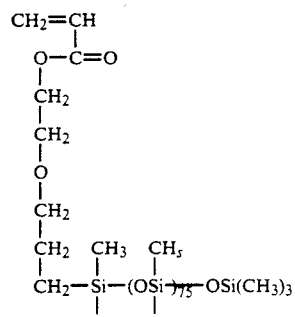
6
-continued
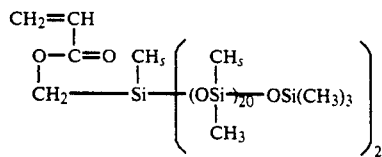
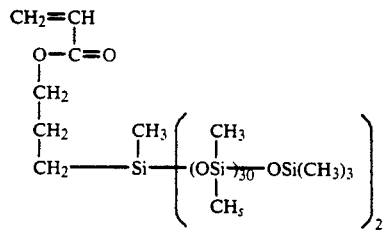
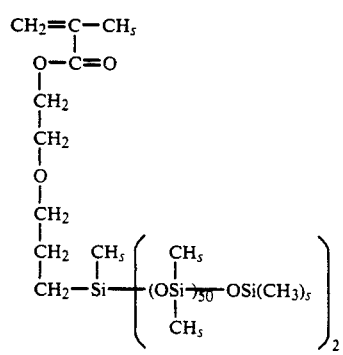
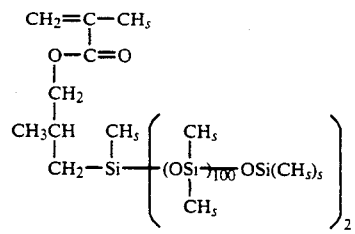
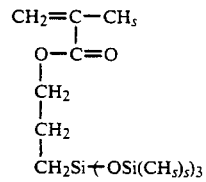
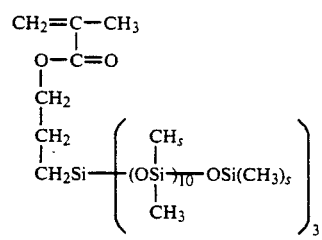
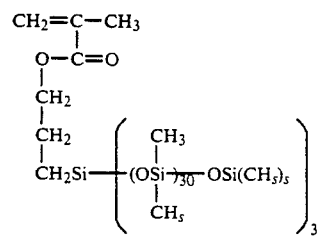

-continued

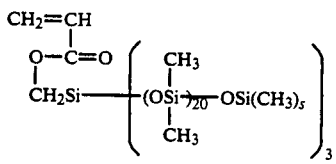

These methylpolysiloxane (meth)acrylate macromonomers may be used either singly or in combination.

As exemplary radical polymerizable monomers copolymerizable with the methylpolysiloxane (meth)acrylate macromonomers, may be mentioned methacrylic acid esters such as methyl methacrylate, ethyl methacrylate, butyl methacrylate, hexyl methacrylate, 2-ethylhexyl methacrylate, octyl methacrylate, decyl methacrylate, dodecyl methacrylate, tridecyl methacrylate, octadecyl methacrylate, 2-hydroxyethyl methacrylate, 3-hydroxypropyl methacrylate, methacrylates having a perfluoroalkyl group having 1-8 carbon atoms, trimethoxysilylpropyl methacrylate and dimethoxymethylsilylpropyl methacrylate; acrylic acid esters such as methyl acrylate, ethyl acrylate, propyl acrylate, butyl acrylate, hexyl acrylate, 2-ethylhexyl acrylate, octyl acrylate, decyl acrylate, dodecyl acrylate, tridecyl acrylate, 2-hydroxyethyl acrylate, 3-hydroxypropyl acrylate and trimethoxysilylpropyl acrylate; styrene and styrene derivatives such as alpha-methylstyrene; vinyl esters such as vinyl acetate, vinyl propionate, vinyl caproate, vinyl caprylate, vinyl laurate and vinyl Versatate; methacrylic acid; acrylic acid; methacrylamide; acrylamide; maleic anhydride; acrylonitrile; and butadiene. These radical polymerizable monomers may be used either singly or in combination.

The wax composition of (a) can be obtained by copolymerizing the methylpolysiloxane (meth)acrylate macromonomer and the radical polymerizable monomer copolymerizable with the macromonomer, which are raw materials for the third component, in the presence of the first component, i.e., dimethylpolysiloxane and/or methylphenylpolysiloxane, the second component, i.e., organic wax, and the radical generator while vigorously stirring at a temperature not lower than the melting point of the second component, the organic wax.

As exemplary radical generators, may be mentioned benzoyl peroxide, butyl perbenzoate, methyl ethyl ketone peroxide, dicumyl peroxide, t-butyl hydroperoxide, 2,2'-azobisisobutyronitrile, 2,2,'-azobisisovaleronitrile, 2,2,'-azobis(2,4-dimethylvaleronitrile) and the like. These radical generators may be used in a range of 0.05-5.0 parts by weight per 100 parts by weight of the methylpolysiloxane (meth)acrylate macromonomer and radical polymerizable monomer.

The polymerization reaction may be conducted either by a process in which a reactor is charged with the third component and radical generator and the contents are maintained at a predetermined reaction temperature with stirring them or by a process in which a reactor is charged with the first component, second component and radical generator, a mixture of the macromonomer and radical polymerizable monomer, which are raw materials for the third component, is added dropwise while maintaining the contents at a predetermined temperature under stirring, and the reaction mixture is aged while further maintaining the same conditions. In any case, the reaction mixture must however be stirred vigorously. For example, in the case where the agitation is conducted by an agitating blade connected to a motor for stirring on a usual scale of a 5-liter or smaller flask, the agitation requires a number of revolutions of at least 200 rpm, preferably at least 300 rpm. In order to vigorously stir, it is also preferable to use a homogenizer. The reaction temperature is set in such a temperature range that it is not lower than the melting point of the organic wax of the second component as described above and a radical generator to be used acts effectively. However, the reaction mixture is generally reacted at a temperature range of 50°-200° C., preferably 70°-150° C. In this case, the reaction is completed for from 30 minutes to 15 hours. It is however necessary to cool the reaction mixture to room temperature while continuing the agitation even after completion of the reaction and then take it out.

In order for the wax composition thus obtained to be dispersed uniformly in the low-viscosity silicone oil, the proportions of the individual components preferably fall within the following ranges:

| | |
|---|---|
| Dimethylpolysiloxane and/or methylphenylpolysiloxane | 45-80 parts by weight |
| Organic wax | 5-35 parts by weight |
| Monomer mixture | 5-50 parts by weight. |

On the other hand, no particular limitation is imposed on the low-viscosity silicone oil of (b). Those having a viscosity of about 50 cSt or lower may be suitably used. The reason is that the resulting emulsified composition feels oily as a result of using a large amount of a silicone oil having a higher viscosity, and such a composition is not preferred from the viewpoint of a feel upon use. As exemplary low-viscosity silicone oil, may be mentioned linear dimethylpolysiloxane having a low degree of polymerization, methylphenylpolysiloxane, cyclic octamethylcyclotetrasiloxane, decamethylcyclopentasiloxane and the like. One or more of these silicone oil may be suitably chosen for use as necessary.

The silicone gel composition contained in the component (A) can be prepared with ease by mixing the wax composition of (a) and the low-viscosity silicone oil of (b) into an intimate dispersion. The mixing proportion by weight of (a) to (b) ranges from 10:90 to 50:50, preferably from 15:85 to 45:55. If the proportion of (a) is lower than the lower limit of this range, a stable and good gel structure cannot be maintained. If the proportion of (a) is higher than the upper limit of this range to the contrary, the resulting emulsified composition feels heavy and oily and hence, the usability and feel upon use become poor. It is therefore not preferred to use the wax composition in such a low or high proportion. The silicone gel composition is incorporated in a proportion of 60-100 wt. % (hereinafter indicated merely by "%") in the component (A). Any proportions lower than 60% result in an emulsified composition poor in feel upon use and lowered in both stability with time and water repellency. It is hence not preferred to incorporate the silicone gel composition in such a low proportion.

The oil-phase component of the component (A) may be added with one or more of oily bases used in usual emulsified compositions in addition to the silicone gel composition so far as they do not impair the uniformity of the oil phase. Any natural animal, vegetable and/or synthetic oils may be used as an oily base. As specific examples thereof, may be mentioned liquid, pasty and solid hydrocarbons such as liquid paraffin and squalane, waxes, higher fatty acids, higher alcohols, esters, glycerides, silicone oils other than (b), etc.

The component (A) is incorporated in a proportion of 30-60% of the whole composition. If the proportion should be lower than 30%, the effects of the inventive composition will be not satisfactorily attained.

The polyoxyalkylene-modified organopolysiloxane surfactant, which is the component (B) in this invention, is represented by the general formula (1) or (2), is designated polyether-modified silicone or alkylpolyether-modified silicone and functions as an emulsifier. These modified-silicones are in the form of a liquid or paste at room temperature and preferably water-insoluble. As examples thereof, may be mentioned "KF-945A" (product of Shin-Etsu Chemical Co., Ltd.) and the like. Since the main chains of these polyoxyalkylene-modified organopolysiloxane surfactants are polysiloxane chains, they are good in both compatibility with the silicone gel composition in the oil-phase component and emulsion stability.

The component (B) is incorporated in a proportion of 0.1-10%, preferably 0.5-5% of the whole composition. Any proportions lower than 0.1% is too small to exhibit sufficiently emulsifying ability. On the other hand, any proportions exceeding 10% result in a too strong interface between water and oil, and the resulting emulsified composition hence feels heavy and sticky. It is therefore not preferred to incorporate the component (B) in such a low or high proportion.

Besides, water of the component (C) is incorporated in a proportion of 5-69.9% of the whole composition.

Furthermore, in the emulsified composition of this invention, may be incorporated in addition to the essential ingredients described above water-phase ingredients and oil-phase ingredients, which are employed conventionally, such as moisturizer, antiseptic, antioxidant, ultraviolet absorbent, nourishing ingredient, perfume base, water-soluble polymer, extender pigment, colored pigment, glitter, organic powder, hydrophobicity-imparted pigment, tar colorant and the like so far as they do not impede the effects of the inventive composition.

The water-in-oil type emulsified composition may be prepared by emulsifying the components in accordance with the conventional process except that the silicone gel composition in the component (A) is prepared in advance to use it in the emulsification, and may suitably be used as a cosmetic base for creams, foundations, etc.

EXAMPLES

The present invention will hereinafter be described more specifically by the following examples. However, it should be borne in mind that this invention is not limited to and by these examples.

REFERENCE EXAMPLE 1

SYNTHESIS OF WAX COMPOSITION

A glass-made reactor equipped with an agitation blade, thermometer, reflux condenser, dropping funnel and nitrogen inlet tube is charged with 300 g of dimethylpolysiloxane ("KF-96", trade name; product of Shin-Etsu Chemical Co., Ltd.) having a viscosity of 6 cSt at 25° C., 120 g of microcrystalline wax ("Besquare 195", trade name; product of Petrolite Company) and 0.5 g of t-butyl perbenzoate ("Perbutyl Z", trade name; product of Nippon Oil & Fats Co., Ltd.). While introducing nitrogen gas, the contents were held at 120° C. in an oil bath to stir them at 600 rpm.

On the other hand, 50 g of methyl methacrylate, 15 g of 2-ethylhexyl acrylate and 35 g of dimethylpolysiloxane methacrylate macromonomer represented by the following formula were thoroughly mixed and added dropwise through the dropping funnel to the mixture over 30 minutes.

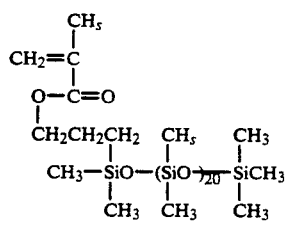

After the addition was completed, the contents were held and stirred for additional 4 hours under the same conditions to age them. The reflux condenser was replaced by a Claisen head to strip the reaction mixture for 2 hours under a reduced pressure of 20 mmHg while holding and stirring it under the same conditions. After completion of the stripping, the oil bath was taken out to cool the reaction mixture to room temperature under stirring, thereby obtaining 504 g of a product in the form of an opaque-white, uniform cream. The wax composition thus obtained was able to be dispersed uniformly in a low-viscosity silicone oil into a gel.

REFERENCE EXAMPLE 2

A wax composition was obtained by using 400 g of dimethylpolysiloxane having a viscosity of 6 cSt, 500 g of microcrystalline wax, 0.8 g of t-butyl perbenzoate, and a mixture of 30 g of methyl methacrylate, 30 g of butyl methacrylate and 40 g of a dimethylpolysiloxane methacrylate macromonomer under the same conditions as in Reference Example 1. The wax composition thus obtained was unable to be dispersed uniformly in a low-viscosity silicone oil.

EXAMPLE 1

Milky water-in-oil type emulsified compositions of their corresponding compositions shown in Table 1 were separately prepared to conduct a test for their stability with time and sensory evaluation. The results are shown in Table 2.

TABLE 1

| Composition (%) | | Inventive composition | | Comparative composition | | |
|---|---|---|---|---|---|---|
| | | 1 | 2 | 1 | 2 | 3 |
| 1 | Wax composition (*1) | 10 | 10 | 10 | — | — |
| 2 | Wax composition (*2) | — | — | — | — | 10 |
| 3 | Dimethylpolysiloxane (6 cSt) | 27 | 14 | 27 | 32 | 27 |
| 4 | Glyceryl trioctanoate | — | 13 | — | — | — |
| 5 | Microcrystalline wax | — | — | — | 2.5 | — |
| 6 | Polyoxyalkylene- (*3) modified organopolysiloxane surfactant | 3 | 3 | — | 3 | 3 |
| 7 | Diglycerol diisostearate | — | — | 3 | — | — |
| 8 | Preservative | 0.2 | 0.2 | 0.2 | 0.2 | 0.2 |

TABLE 1-continued

| Composition (%) | Inventive composition | | Comparative composition | | |
|---|---|---|---|---|---|
| | 1 | 2 | 1 | 2 | 3 |
| 9  Purified water | Balance | | | | |

*1: Obtained in Reference Example 1.
*2: Obtained in Reference Example 2.
*3: In the general formula (1), $R_1 = G_1 = G_2 = CH_3$, a = 20-30, b = 1-5, $Q_1$ = $(CH_2)_3$, m = 2-5, n = 0 and $R_3$ = H.

Preparation Process

A: A part of the component 9 is gradually added to the component 6 or 7 to stir and mix them, thereby obtaining a gel-like emulsion.

B: Their corresponding components 1-5 are mixed with one another and heated to 70° C. into a solution.

C: The component 8 is mixed with the remainder of the component 9, and the mixture was heated to 70° C. into a solution.

D: After the emulsion in the step A is added to the solution in the step B to homogenize the mixture, the solution in the step C is added to emulsify nd cool them, thereby obtaining a water-in-oil type emulsified composition.

EVALUATING METHODS

Stability with time

Portions of each emulsified composition were respectively left to stand in constant temperature baths controlled at 50° C., 40° C. and 5° C. to observe their states after 1 day, 1 week, 2 weeks and 4 weeks. The stability with time was evaluated in accordance with the following standard.

○:No change was observed on its state;
△:Separation or cohesion was slightly observed;
x: Separation or cohesion was markedly observed.

Sensory evaluation

Each of the emulsified compositions was evaluated in accordance with the following standard whether it was not rough to the touch, spread well upon application, did not feel oily upon and sticky after application, and had good water resistance.

◎:Excellent;
○:Good;
△:Comparable;
x:Poor

TABLE 2

| Composition (%) | | | Inventive composition | | Comparative composition | | |
|---|---|---|---|---|---|---|---|
| | | | 1 | 2 | 1 | 2 | 3 |
| Stability with time | After 1 day | 50° C. | ○ | ○ | △ | x | ○ |
| | | 40° C. | ○ | ○ | △ | x | ○ |
| | | 5° C. | ○ | ○ | ○ | x | ○ |
| | After 1 week | 50° C. | ○ | ○ | x | x | △ |
| | | 40° C. | ○ | ○ | x | x | △ |
| | | 5° C. | ○ | ○ | △ | x | ○ |
| | After 2 weeks | 50° C. | ○ | ○ | x | x | x |
| | | 40° C. | ○ | ○ | x | x | x |
| | | 5° C. | ○ | ○ | x | x | △ |
| | After 4 weeks | 50° C. | ○ | ○ | x | x | x |
| | | 40° C. | ○ | ○ | x | x | x |
| | | 5° C. | ○ | ○ | x | x | x |
| Sensory evaluation | No rough feeling | | ◎ | ◎ | ◎ | x | x |
| | Spreading upon application | | ◎ | ◎ | x | x | x |
| | No oily feeling upon application | | ◎ | ◎ | △ | x | x |
| | No sticky feeling | | ◎ | ◎ | x | x | x |
| | after application Water resistance | | ◎ | ◎ | ○ | x | △ |

As apparent from Table 2, it was observed that the water-in-oil emulsified compositions according to this invention made no change in their states in each case and exhibited high stability. To the contrary, the separation of the oily base was observed in the comparative compositions, and they were hence poor in stability.

In addition, the emulsified compositions of this invention were excellent in feel upon use because they were not rough to the touch, were smooth, spread well upon application, felt neither oily nor sticky and were pleasantly dry to the touch, and moreover, the oil film formed after application had very high water resistance so that the film could stay on the skin in an excellent condition for a prolonged period.

Incidentally, since a uniform silicone gel composition was not obtained in the comparative composition 3, the oil phase lacked uniformity. Therefore, this emulsified composition lacked smoothness, was rough to the touch and hence poor in feel upon use.

EXAMPLE 2

CREAM

| (Formulation) | | (%) |
|---|---|---|
| 1 | Wax composition (obtained in Reference Example 1) | 15 |
| 2 | Dimethylpolysiloxane (6 cSt) | 22 |
| 3 | Polyoxyalkylene-modified organopolysiloxane surfactant* | 3 |
| 4 | Preservative | 0.2 |
| 5 | Purified water | Balance |

*: In the general formula (1), $R_1 = G_1 = G_2 = CH_3$, a = 20-30, b = 1-5, $Q_1$ = $(CH_2)_3$, m = 2-5, n = 0 and $R_3$ = H.

Preparation Process

A: A part of the component 5 is gradually added to the component 3 to stir and mix them, thereby obtaining a gel-like emulsion.

B: The components 1 and 2 are mixed with each other and heated to 70° C. into a solution.

C: The component 4 is mixed with the remainder of the component 5, and the mixture is heated to 70° C. into a solution.

D: After the emulsion in the step A is added to the solution in the step B to homogenize the mixture, the solution in the step C is added to emulsify and cool them, thereby obtaining a cream.

The cream of this invention, which had been obtained in the above-described manner, was excellent in stability with time, gave a favorable dry feel upon use because it felt neither oily nor sticky, and also had good water repellency.

EXAMPLE 3

FOUNDATION (Formulation)

| | | (parts by weight) |
|---|---|---|
| 1 | Wax composition (obtained in Reference Example 1) | 15 |
| 2 | Dimethylpolysiloxane (6 cSt) | 20 |
| 3 | Polyoxyalkylene-modified organo-polysiloxane surfactant* | 3 |
| 4 | Preservative | 0.2 |
| 5 | Purified water | 66.8 |
| 6 | Titanium dioxide | 12 |
| 7 | Mica | 3.5 |
| 8 | Titanated mica | 0.5 |
| 9 | Inorganic pigment | 3.5 |
| 10 | Squalane | 0.5 |
| 11 | Dimethylpolysiloxane (6 cSt) | 20 |

*: In the general formula (1), $R_1 = G_1 = G_2 = CH_3$, $a = 20-30$, $b = 1-5$, $Q_1 = (CH_2)_3$, $m = 2-5$, $n = 0$ and $R_3 = H$.

Preparation Process

A: The component 6–11 are mixed with one another, and the mixture is ground in a roll mill.

B: The components 1 and 3 are dissolved in a part of the component 2 while heating them to 70° C.

C: The component 4 is mixed with the component 5, and the mixture is heated to 70° C. into a solution.

D: The solution in the step C is added to the solution in the step B to emulsify and cool them.

E: The mixture in the step A is mixed with the remainder of the component 2, and the mixture is added to the emulsion in the step D to mix them, thereby obtaining a foundation.

The foundation of this invention, which had been obtained in the above-described manner, was excellent in stability with time, gave a favorable dry feel upon use and permitted the formation of a makeup film high in water repellency.

EXAMPLE 4

CREAM (Formulation)

| | | (%) |
|---|---|---|
| 1 | Wax composition (obtained in Reference Example 1) | 15 |
| 2 | Dimethylpolysiloxane (6 cSt) | 21 |
| 3 | Polyoxyalkylene-modified organo-polysiloxane surfactant* | 3 |
| 4 | Liquid paraffin | 1 |
| 5 | Preservative | 0.2 |
| 6 | Purified water | Balance |

*: In the general formula (2), $R_1 = G_3 = G_4 = CH_3$, $a = 20-60$, $b = 1-10$, $c = 2-10$, $Q_1 = (CH_2)_3$, $m = 2-10$, $n = 2$, $R_3 = H$ and $R_4 = C_{16}H_{33}$.

Preparation Process

A: A part of the component 6 is gradually added to the components 3 and 4 to stir and mix them, thereby obtaining a gel-like emulsion.

B: The components 1 and 2 are mixed with each other and heated to 70° C. into a solution.

C: The component 5 is mixed with the remainder of the component 6, and the mixture is heated to 70° C. into a solution.

D: After the emulsion in the step A is added to the solution in the step B to homogenize the mixture, the solution in the step C is added to emulsify and cool them, thereby obtaining a cream.

The cream of this invention, which had been obtained in the above-described manner, was excellent in stability with time, gave a favorable dry feel upon use because it felt neither oily nor sticky, and also had good water repellency.

EXAMPLE 5

CREAM (Formulation)

| | | (%) |
|---|---|---|
| 1 | Wax composition (obtained in Reference Example 1) | 15 |
| 2 | Dimethylpolysiloxane (6 cSt) | 20 |
| 3 | Polyoxyalkylene-modified organo-polysiloxane surfactant* | 3 |
| 4 | Glyceryl trioctanoate | 2 |
| 5 | Preservative | 0.2 |
| 6 | Purified water | Balance |

*: In the general formula (1), $R_1 = CH_3$, $G_1 = G_2 = R_2$, $Q_1 = (CH_2)_3$, $m = 8-12$, $n = 1-3$, $R_3 = H$, $a = 10-20$ and $b = 0$.

Preparation Process

A: A part of the component 6 is gradually added to the components 3 and 4 to stir and mix them, thereby obtaining a gel-like emulsion.

B: The components 1 and 2 are mixed with each other and heated to 70° C. into a solution.

C: The component 5 is mixed with the remainder of the component 6, and the mixture is heated to 70° C. into a solution.

D: After the emulsion in the step A is added to the solution in the step B to homogenize the mixture, the solution in the step C is added to emulsify and cool them, thereby obtaining a cream.

The cream of this invention, which had been obtained in the above-described manner, was excellent in stability with time, gave a favorable dry feel upon use because it felt neither oily nor sticky, and also had good water repellency.

EXAMPLE 6

CREAM (Formulation)

| | | (%) |
|---|---|---|
| 1 | Wax composition (obtained in Reference Example 1) | 15 |
| 2 | Dimethylpolysiloxane (6 cSt) | 20 |
| 3 | Polyoxyalkylene-modified organo-polysiloxane surfactant* | 3 |
| 4 | Glyceryl trioctanoate | 2 |
| 5 | Preservative | 0.2 |
| 6 | Purified water | Balance |

*: In the general formula (1), $R_1 = G_1 = CH_3$, $G_2 = R_2$ $Q_1 = (CH_2)_3$, $m = 8-12$, $n = 0$, $R_3 = H$, $a = 8-10$ and $b = 0$.

Preparation Process

A: A part of the component 6 is gradually added to the components 3 and 4 to stir and mix them, thereby obtaining a gel-like emulsion.

B: The components 1 and 2 are mixed with each other and heated to 70° C. into a solution.

C: The component 5 is mixed with the remainder of the component 6, and the mixture is heated to 70° C. into a solution.

D: After the emulsion in the step A is added to the solution in the step B to homogenize the mixture, the solution in the step C is added to emulsify and cool them, thereby obtaining a cream.

The cream of this invention, which has been obtained in the above-described manner, was excellent in stability with time, gave a favorable dry feel upon use because it felt neither oily nor sticky, and also had good water repellency.

EXAMPLE 7

CREAM

| (Formulation) | | (%) |
| --- | --- | --- |
| 1 | Wax composition (obtained in Reference Example 1) | 15 |
| 2 | Dimethylpolysiloxane (6 cSt) | 15 |
| 3 | Polyoxyalkylene-modified organopolysiloxane surfactant* | 3 |
| 4 | Glyceryl trioctanoate | 7 |
| 5 | Preservative | 0.2 |
| 6 | Purified water | balance |

*: In the general formula (2), $R_1 = G_3 = G_4 = CH_3$, $Q_1 = (CH_2)_3$, m = 8-11, n = 0, $R_3$ = H, $Q_2 = (CH_2)_3$, $R_5 = C_{18}H_{35}$, a = 10-14, b = 2-4 and c = 8-12.

Preparation Process

A: A part of the component 6 is gradually added to the components 3 and 4 to stir and mix them, thereby obtaining a gel-like emulsion.

B: The components 1 and 2 are mixed with each other and heated to 70° C. into a solution.

C: The component 5 is mixed with the remainder of the component 6, and the mixture is heated to 70° C. into a solution.

D: After the emulsion in the step A is added to the solution in the step B to homogenize the mixture, the solution in the step C is added to emulsify and cool them, thereby obtaining a cream.

The cream of this invention, which had been obtained in the above-described manner, was excellent in stability with time, gave a favorable dry feel upon use because it felt neither oily nor sticky, and had good water repellencey.

What is claimed is:

1. A water-in-oil type emulsified composition comprising the following components (A) through (C):

(A) 30-60 wt. % of an oil-phase component comprising 60-100 wt. % of a silicone gel composition composed of:

(a) a wax composition obtained by polymerizing a mixture of at least one macromonomer selected from the group consisting of methylpolysiloxane (meth)acrylate macromonomers, which contain one (meth)acrylate group and at least three methylsiloxy groups per molecule, and at least one radical polymerizable monomer copolymerizable with the macromonomers in the presence of dimethylpolysiloxane and/or methylphenylpolysiloxane and an organic wax using a radical generator, said wax composition being dispersed in a low-viscosity silicone oil; and (b) a low-viscosity silicone oil;

(B) 0.1-10 wt. % of a polyoxyalkylene-modified organopolysiloxane surfactant represented by the general formula (1) or (2):

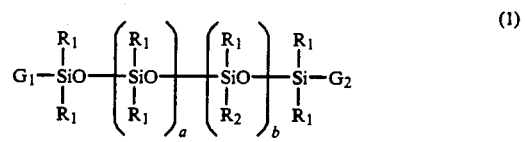

wherein $R_1$ denotes an alkyl group having 1-5 carbon atoms or a phenyl group, $R_2$ represents $-Q_1O(C_2H_4O)_m(C_3H_6O)_nR_3$, in which $Q_1$ means a divalent hydrocarbon group having 1-5 carbon atoms, $R_3$ denotes a hydrogen atom, an alkyl group having 1-5 carbon atoms or an acetyl group, and m and n stand for an integer of one or more and zero or more, respectively, $G_1$ and $G_2$ may be identical to or different from each other and mean individually $R_1$ or $R_2$, and a and b stand for an integer of zero or more, respectively, with the proviso that in case of b being zero, at least one of $G_1$ and $G_2$ means $R_2$:

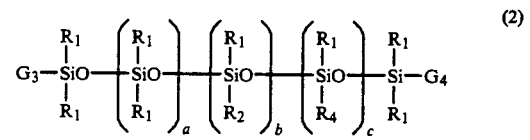

wherein $R_1$, $R_2$, a and b have the same meaning as defined above, $R_4$ represents an alkyl group having 2-20 carbon atoms or $-Q_2OR_5$, in which $Q_2$ means a divalent hydrocarbon group having 1-4 carbon atoms, $R_5$ denotes a hydrocarbon group having 8-30 carbon atoms, $G_3$ and $G_4$ may be identical to or diferent from each other and mean individual $R_1$, $R_2$ or $R_4$, and c stand for an integer of zero or more with the proviso that in case of b being zero, at least one of $G_3$ and $G_4$ means $R_2$, and in case of c being zero, at least one of $G_3$ and $G_4$ means $R_4$; and (C) 5-69.9 wt. % of water.

2. The emulsified composition according to claim 1, wherein the dimethylpolysiloxane or methylphenylpoly-siloxane constituting the wax composition of (a) in the component (A) is represented by the following general formula:

$(CH_3)_p(C_6H_5)_qSiO_{(4-p-q)/2}$ wherein p and q satisfy the following relationship:

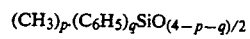

3. The emulsified composition according to claim 2, wherein the dimethylpolysiloxane or methylphenylpolysiloxane is linear, cyclic or branched.

4. The emulsified composition according to claim 1, wherein the organic wax is a natural or synthetic, organic solid substance selected from the group consisting of animal waxes, vegetable waxes, petroleum waxes and synthetic waxes.

5. The emulsified composition according to claim 1, wherein the weight fraction of the methylpolysiloxane (meth)acrylate macromonomer in the wax composition is 5-90 wt. %.

6. The emulsified composition according to claim 1, wherein the macromonomer is represented by the general formula (3):

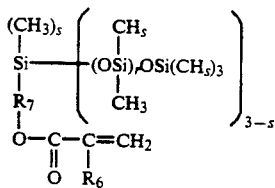
(3)

wherein s stands for 0, 1 or 2, r means an average polymerization degree and is 0–200 when s is 0, 1–200 when s is 1, or 2–200 when s is 2, $R_6$ denotes a hydrogen atom or a methyl group, and $R_7$ means a divalent hydrocarbon group having 1–6 carbon atoms, which may be interrupted by an oxygen atom.

7. The emulsified composition according to claim 1, wherein the radical generator is selected from the group consisting of benzoyl peroxide, butyl perbenzoate, methyl ethyl ketone peroxide, dicumyl peroxide, t-butyl hydroperoxide, 2,2,'-azobis-isobutyronitrile, 2,2'-azobisisovaleronitrile, and 2,2'-azobis(2,4-dimethylvaleronitrile) and used in a range of 0.05–5.0 parts by weight per 100 parts by weight of the methylpolysiloxane (meth)acrylate macromonomer and radical polymerizable monomer.

8. The emulsified composition according to claim 1, wherein the proportions of the individual components in the wax composition fall within the following ranges:

| | |
|---|---|
| Dimethylpolysiloxane and/or methylphenylpolysiloxane | 45–80 parts by weight |
| Organic wax | 5–35 parts by weight |
| Monomer mixture | 5–50 parts by weight. |

9. The emulsified composition according to claim 1, wherein the low-viscosity silicone oil has a viscosity of 50 cSt or lower.

10. The emulsified composition according to claim 1, wherein the low-viscosity silicone oil is selected from the group consisting of linear dimethylpolysiloxane having a low degree of polymerization, methylphenylpolysiloxane, cyclic octamethylcyclotetrasiloxane and decamethylcyclopenta-siloxane.

11. The emulsified composition according to claim 1, wherein the mixing proportion by weight of (a) to (b) in the component (A) ranges from 10:90 to 50:50.

12. The emulsified composition according to claim 1, wherein the mixing proportion by weight of (a) to (b) in the component (A) ranges from 15:85 to 45:55.

13. The emulsified composition according to claim 1, wherein the proportion of the component (B) is 0.5–5 wt. %.

* * * * *

UNITED STATES PATENT AND TRADEMARK OFFICE
CERTIFICATE OF CORRECTION

PATENT NO. : 5,262,087
DATED : November 16, 1993
INVENTOR(S) : Kiyomi TACHIBANA et al.

It is certified that error appears in the above-identified patent and that said Letters Patent is hereby corrected as shown below:

On the title page, insert [73] Assignee

--SHIN-ETSU CHEMICAL CO., LTD., OF Tokyo, JAPAN--

Signed and Sealed this

Eleventh Day of April, 1995

Attest:

BRUCE LEHMAN

Attesting Officer

Commissioner of Patents and Trademarks